United States Patent
Murray

(10) Patent No.: US 8,185,314 B2
(45) Date of Patent: May 22, 2012

(54) METHOD AND SYSTEM FOR DETERMINING DYNAMIC PERMEABILITY OF GAS HYDRATE SATURATED FORMATIONS

(75) Inventor: Doug Murray, Beijing (CN)

(73) Assignee: Schlumberger Technology Corporation, Sugar Land, TX (US)

( * ) Notice: Subject to any disclaimer, the term of this patent is extended or adjusted under 35 U.S.C. 154(b) by 640 days.

(21) Appl. No.: 12/027,267

(22) Filed: Feb. 7, 2008

(65) Prior Publication Data

US 2008/0221799 A1 Sep. 11, 2008

Related U.S. Application Data

(60) Provisional application No. 60/889,546, filed on Feb. 13, 2007.

(51) Int. Cl.
*G01N 15/08* (2006.01)
(52) U.S. Cl. ........... 702/12; 702/6; 702/7; 702/11
(58) Field of Classification Search .......... 702/6–7, 702/11
See application file for complete search history.

(56) References Cited

U.S. PATENT DOCUMENTS

| | | | | |
|---|---|---|---|---|
| 3,242,422 | A * | 3/1966 | Bloembergen | 324/303 |
| 4,933,638 | A | 6/1990 | Kenyon et al. | |
| 5,023,551 | A | 6/1991 | Kleinberg et al. | |
| 5,486,761 | A | 1/1996 | Sezginer | |
| 6,111,409 | A * | 8/2000 | Edwards et al. | 324/303 |

FOREIGN PATENT DOCUMENTS

| | | |
|---|---|---|
| WO | 2006/031872 | 3/2006 |
| WO | WO2006031872 | * 3/2006 |
| WO | WO 2006031872 A1 | * 3/2006 |

OTHER PUBLICATIONS

Kenyon, W.E., 1992, "Nuclear magnetic resonance as a petrophysical measurement", Nuclear Geophysics, 6, 153-171.

Timur, A., 1969, "Pulsed Nuclear Magnetic Resonance Studies of Porosity, Movable Fluid, and Permeability of Sandstones", JPT, 21, 775-786.

Murray, D., Fukuhara, M., Khong, C.K., Namikawa, T. and Yamamoto, K., 2006, "Permeability Estimates in Gas Hydrate Reservoirs of the Nankai Trough", 47th Annual SPWLA Symposium.

Kleinberg, R.L., Flaum, C. and Collett, T.S., 2005, "Magnetic resonance log of Mallik 5L38: Hydrate saturation, growth habit, and relative permeability", Scientific Results from the Mallik 2002 Gas Hydrate Production Research Well, Mackenzie Delta, Northwest Territories, Canada, Bulletin 585, Geological Survey of Canada, Ottawa, S.R. Dallimore and T.S. Collett (Editors).

Murray, D., Kleinberg, R., Sinha, B., Fukuhara, M., Endo, T. and Namikawa, T., 2005, "Formation Evaluation of Gas Hydrate Reservoirs", 46th Annual SPWLA Symposium.

(Continued)

*Primary Examiner* — Drew A Dunn
*Assistant Examiner* — Mischita Henson
(74) *Attorney, Agent, or Firm* — Jianguang Du; Jody DeStefanis; Jeff Griffin

(57) ABSTRACT

A method and system for determining dynamic permeability of gas hydrate formations including deploying a tool within a wellhole configured for magnetic resonance measurements, determining permeability of a formation at or near zero saturation of the gas hydrate and deriving the relationship between permeability and gas hydrate saturation for the formation.

18 Claims, 4 Drawing Sheets

OTHER PUBLICATIONS

Herron, M.M., Johnson, D.L., and Schwartz, L.M., 1998, "A Robust Permeability Estimator for Siliciclastics,", SPE 49301 paper presented at the 1998 Annual Technical Conference and Exhibition of the Society of Petroleum Engineers, New Orleans, Louisiana, Sep. 27-30, 1998.

M. W. Lee, T. S. Collett, "Controls on the Physical Properties of Gas-Hydrate-Bearing Sediments Because of the Interaction Between Gas Hydrate and Porous Media", Internet Citation, XP002357961, Retrieved from the Internet: URL: Reston, Virginia, http://pubs.usgs.gov/sir/2005/5143/pdf/SIR-5143.pdf, Aug. 2005.

Jacobsen S, et al., "Producibility Prediction in Gas Sands Through Effective Integration of NMR, Resistivity and Porosity Log Data", Society of Professional Well Log Analysts., SPWLA Annual Loggign Symposium Transactions, SPWLA, US, vol. 47, Jan. 1, 2006 pp. 1-24.

* cited by examiner

METHOD AND SYSTEM FOR DETERMINING DYNAMIC PERMEABILITY OF GAS HYDRATE SATURATED FORMATIONS

CROSS-REFERENCE TO RELATED APPLICATION

This application relates to and claims the benefit under 35 U.S.C. §119(e) of applicant's U.S. Provisional Application Ser. No. 60/889,546 entitled "Determining Dynamic Permeability of Hydrocarbon Reservoirs," filed Feb. 13, 2007. The disclosure of this Provisional Application is hereby incorporated herein by reference in its entirety.

BACKGROUND

This invention is generally related to a method and system for recovering gas hydrates from subterranean formations. More particularly, this invention relates to a method and system for determining the intrinsic permeability of subterranean formations having gas hydrates sequestered therein.

Permeability of a material is a measure of the material's ability to transmit fluids through its pore spaces and is inversely proportional to the flow resistance offered by the material. Typically, permeability is determined by taking core samples from a hydrocarbon formation and applying permeability measurement techniques to the core samples. When obtainable, cores of the formation provide important data concerning permeability. However, cores are difficult and expensive to obtain, and core analysis is time consuming and provides information about very small sample volumes. In addition, cores, when brought to the surface, may not adequately represent downhole conditions. Thus, in-situ determinations of permeability that can quickly provide permeability information over large portions of the formation would be highly desirable.

Nuclear magnetic resonance (NMR) measurements are used to infer formation permeability. In particular, it is known that the strength of a NMR signal is directly proportional to the number of resonated spins present in a probed volume. Because hydrogen is the nucleus of choice in most borehole measurements, and because NMR tools can be tuned in frequency to resonate a particular nuclear species, the signal amplitude of a tuned tool can be arranged to measure the number of hydrogen atoms in the formation. The number of hydrogen atoms in the formation in turn is related to fluid filled porosity.

In addition to being sensitive to hydrogen density, NMR tools are sensitive to the environment of the hydrogen being probed. For example, hydrogen in a bound or "irreducible" fluid typically has a spin-lattice relaxation time ($T_2$) in the milliseconds to tens of milliseconds, while free or producible fluid has a $T_2$ in the range of tens to hundreds of milliseconds. Thus, in addition to correlating well porosity, the measurements resulting from the NMR sequences applied to a formation provide information which may be correlated with the "free fluid index", permeability, and residual oil saturation.

Currently, NMR measurements in the borehole are being made via a Combinable Magnetic Resonance tool or "CMR" (a trademark of Schlumberger), and a Magnetic Resonance Expert tool or "MR Scanner" (also a trademark of Schlumberger) which features a gradient magnetic field and multiple frequencies of operation; both of which are commercially successful tools of Schlumberger, the assignee hereof. Details of NMR borehole tools may be seen with reference to U.S. Pat. No. 4,933,638 to Kenyon et al., U.S. Pat. No. 5,023,551 to Kleinberg et al., and U.S. Pat. No. 5,486,761 to Sezginer, all of which are hereby incorporated by reference herein in their entireties.

As disclosed herein, the subject formations may be saturated with hydrates, such as methane hydrates. A gas hydrate is a crystalline solid that is a cage-like lattice of a mechanical intermingling of gas molecules in combination with molecules of water. The name for the parent class of compounds is "clathrates" which comes from the Latin word meaning "to enclose with bars." The structure is similar to ice but exists at temperatures well above the freezing point of ice. Gas hydrates include carbon dioxide, hydrogen sulfide, and several low carbon number hydrocarbons, including methane. The disclosure herein relates to the recovery of methane from subterranean methane hydrates.

Methane hydrates are known to exist is large quantities in two types of geologic formations: (1) in permafrost regions where cold temperatures exist in shallow sediments and (2) beneath the ocean floor at water depths greater than 500 meters where high pressures prevail. Large deposits of methane hydrates have been located in the United States in Alaska, the west coast from California to Washington, the east coast in water depths of 800 meters, and in the Gulf of Mexico.

A U.S. Geological Survey study estimates that in-place gas resources within gas hydrates consist of about 200,000 trillion cubic feet which dwarfs the previously estimated 1,400 trillion cubic feet of conventional recoverable gas reserves in the United States. Worldwide, estimates of the natural gas potential of gas hydrates approach 400 million trillion cubic feet.

Natural gas is an important energy source in the United States. It is estimated that by 2025 natural gas consumption in the United States will be nearly 31 trillion cubic feet. Given the importance and demand for natural gas the development of new cost-effective sources can be a significant benefit for American consumers.

The determination of permeability and other hydraulic properties of formations surrounding boreholes is very useful in gauging the producibility of formations, and in obtaining an overall understanding of the structure of the formations. For the reservoir engineer, permeability is generally considered a fundamental reservoir property, the determination of which is at least equal in importance with the determination of porosity, fluid saturations, and formation pressure.

SUMMARY OF THE DISCLOSURE

A method and system disclosed herein are directed at the in-situ characterization of formations using magnetic resonance measurements to determine the dynamic relationship between intrinsic permeability of a formation and gas hydrate saturation. The present inventor has found that an understanding of such a intrinsic permeability-gas hydrate saturation relationship will provide useful information with respect to the production of gas hydrates from subterranean reservoirs.

In one aspect disclosed herein, a method is provided for determining dynamic permeability of gas hydrate formations by in-situ evaluation. A tool configured for magnetic resonance measurements is deployed within a well hole, and measurements are acquired with respect to permeability of the surrounding formations at multiple depths such that the measured permeabilities relate to different fluid saturations of a hydrocarbon of interest in the formations. Permeability of the formations at or near zero saturation of the hydrocarbon of interest is determined. A relationship between permeability and gas hydrate saturation for the formations is derived utilizing the acquired data. As disclosed herein, the hydrocarbon of interest may be methane hydrate.

In other aspects herein, the tool comprises at least one of a wireline and a slickline tool. In yet other aspects, the tool is a logging-while-drilling (LWD) tool.

The permeability of the formation at or near zero gas hydrate saturation may be determined using geochemical measurements. The data relating to the magnetic resonance measurements may be transmitted to the surface for processing, and the surface processing may include real time processing of the data.

Other aspects disclosed herein include a system for determining dynamic permeability of gas hydrate formations by in-situ evaluation, comprising a tool configured for magnetic resonance measurements within a wellhole to measure permeability of a formation at multiple depths such that the measured permeabilities relate to different fluid saturations of a gas hydrate of interest in the formation; and a processor configured for determining permeability of the formation at or near zero saturation of the gas hydrate of interest and deriving the relationship between permeability and gas hydrate saturation for the formation.

Other features and advantages of the present invention will become apparent from the following description of the invention which refers to the accompanying drawings.

THE DRAWINGS

Figure 3:
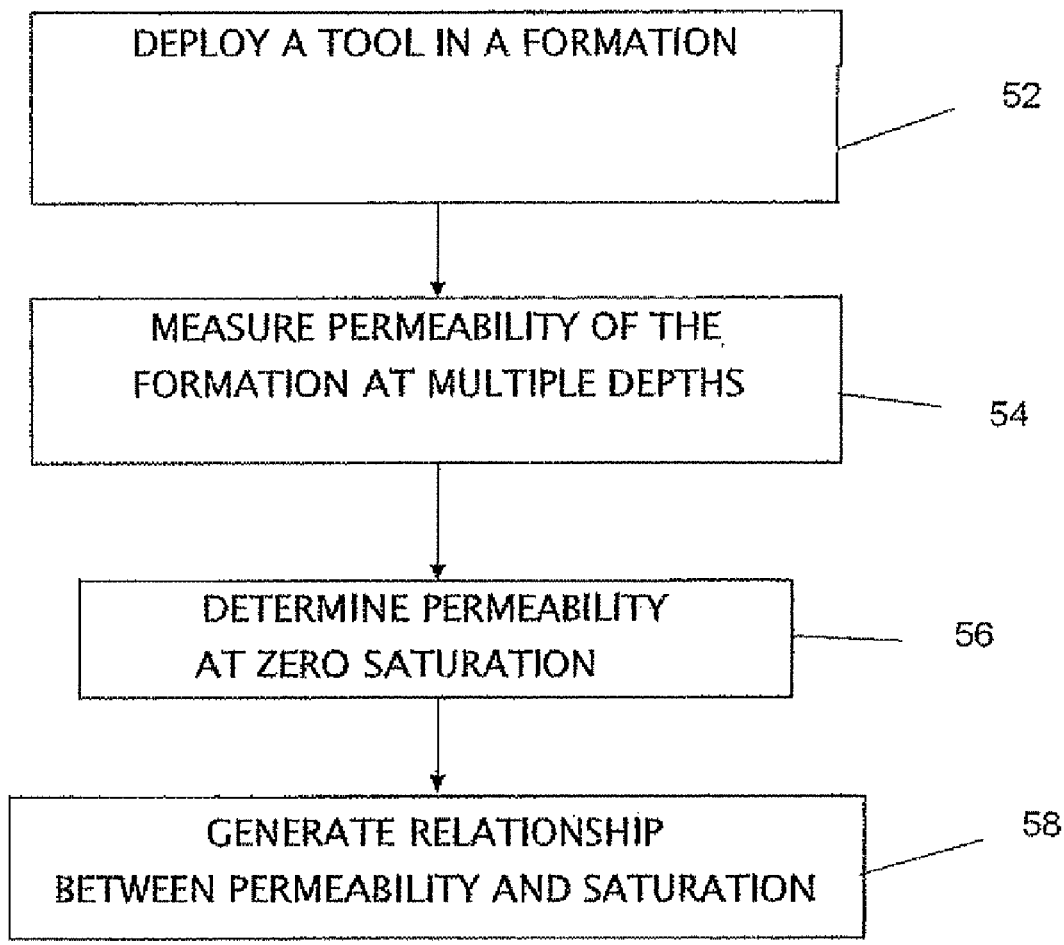

FIG. 3 outlines steps in one method according to the present disclosure; and

Figure 4:
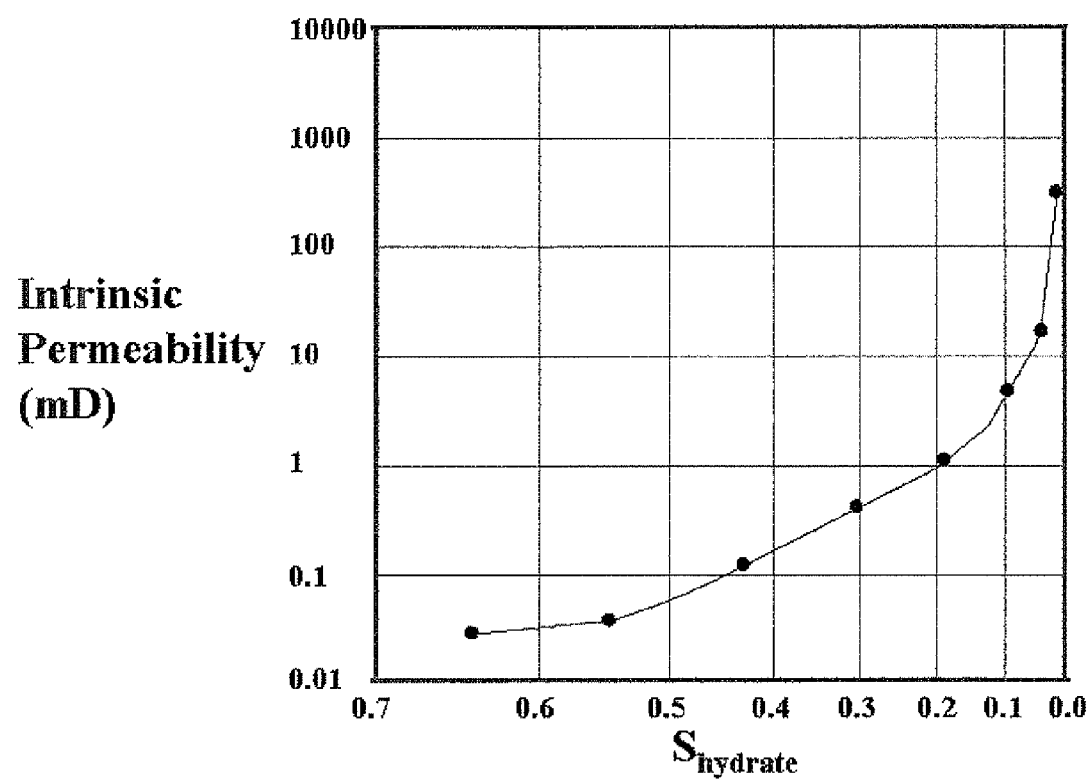

FIG. 4 is a graphical representation of a simulated dynamic relationship between intrinsic permeability of a formation and gas hydrate saturation of the formation.

DETAILED DESCRIPTION

Figure 1:
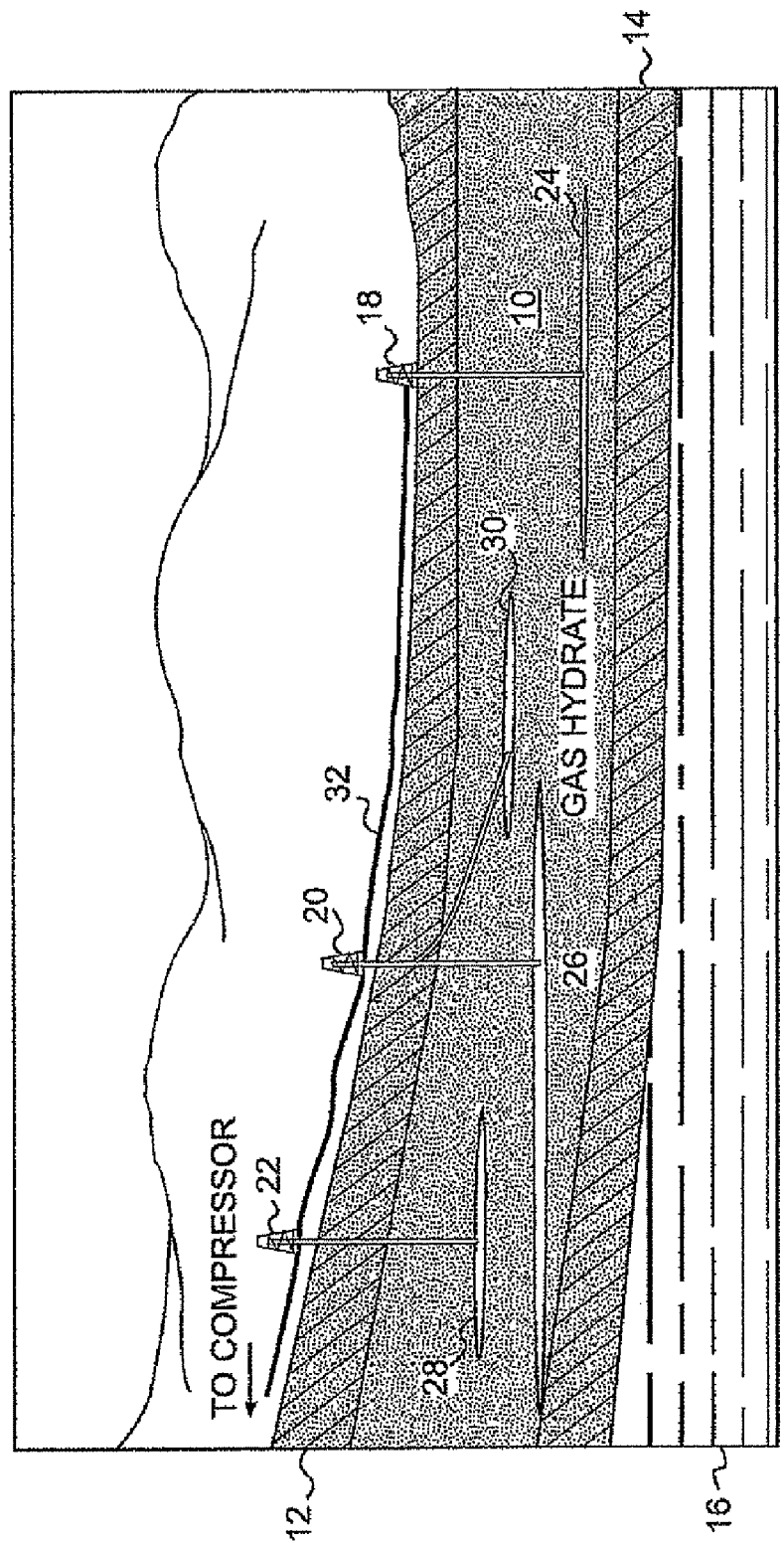
FIG. 1 is a pictorial view of one operational context of the invention such as a geological region of permafrost in Alaska where gas hydrates are know to exist.

Turning now to the drawings wherein like numerals indicate like parts, FIG. 1 discloses a pictorial representation of one operating context of the invention. In this view a band of gas hydrate 10 lies in a rather shallow geologic zone beneath a permafrost layer 12 such as exists in Alaska. Other earth formations 14 and/or aquifer regions 16 can exist beneath the gas hydrate.

In order to recover sequestered methane gas from within the gas hydrate zone one or more wells 18, 20 and/or 22 are drilled through the permafrost 12 and into the gas hydrate zone 10. Usually a casing is cemented within the well and one or more windows are opened directly into the hydrate zone to depressurize irregular regions of the gas hydrate represented by irregular production zones 24, 26, 28 and 30 extending away from distal terminals of the wells. Although a single well is shown drilled from a single derrick illustrated at 18 and 22 it is envisioned that directional drilling as illustrated at derrick 20 and zone 30 will be a more common practice to extend the scope of a drilling operation.

Once one or more wells are drilled, pressure is relieved from the gas hydrate zone around the well and the methane gas and water molecules will separate and enter the wells. The gas can then be separated from the water and allowed to rise to the surface or is pumped to the surface along with water and separated and fed along a pipeline 32 to a compressor station not shown.

Figure 2:
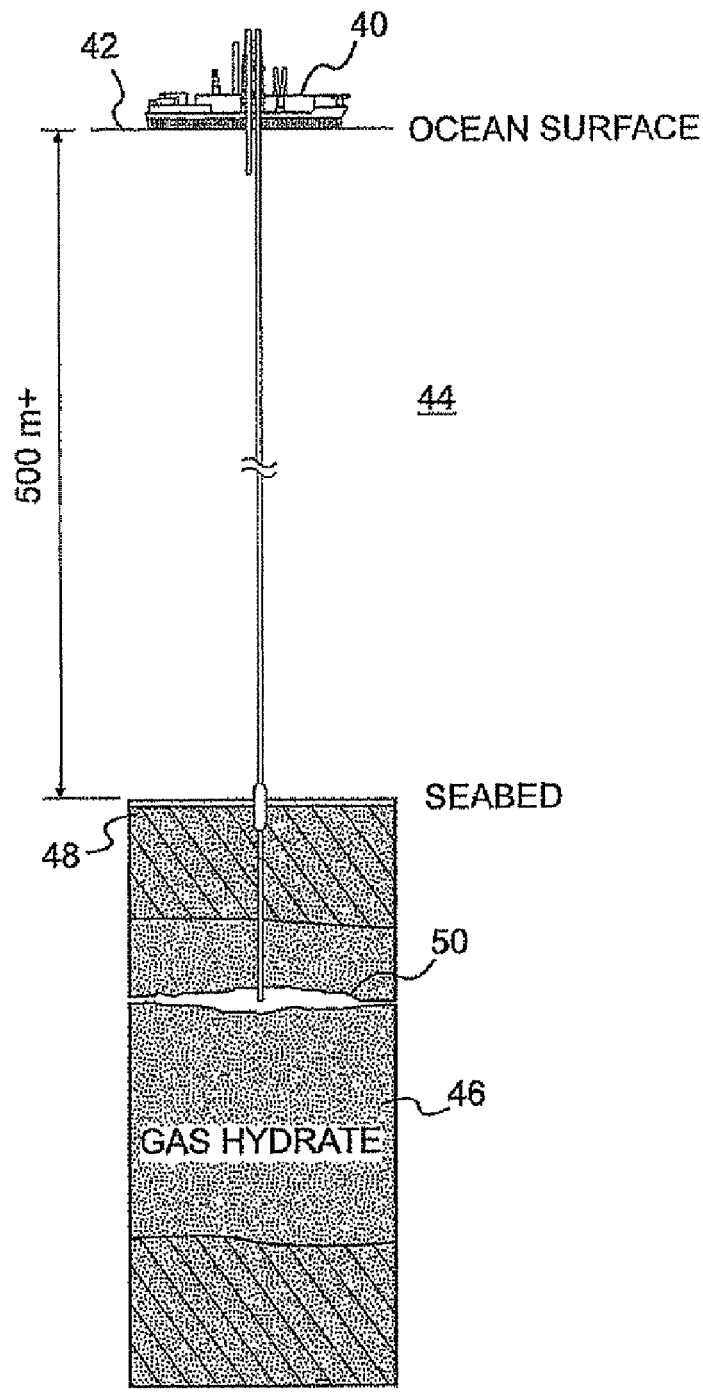
FIG. 2 is a pictorial view of another context or geological region of gas hydrates beneath offshore regions of the United States in water greater than 500 meters in depth.

An alternative operating context of the invention is illustrated in FIG. 2 where a drillship 40 is shown floating upon the surface 42 of a body of water 44 such as the Gulf of Mexico. In this marine environment pressures in water depths approximately greater that 500 meters have been conducive to the formation again of geologic layers of gas hydrates 46, such as methane hydrates, beneath the seabed 48.

Offshore drilling in water depths of 500 meters or more is now technically possible so that drilling into the offshore gas hydrate formations 46 and cementing a casing into a well hole offshore to form a production strata 50 is another source of production of methane from a gas hydrate formation. Again, directional drilling from a subsea template enables fifty or more wells to be drilled from a single drillship location.

In-situ values of the intrinsic permeability of gas hydrate saturated rock are important input parameters for reservoir characterization, reservoir simulation, the understanding of hydrate production, and the determination of the most economical method of production. In the present invention, original in-situ intrinsic permeability can be reasonably estimated from a derivation of magnetic resonance log data. The nuclear magnetic resonance log measurement is typically presented as a distribution of magnetic resonance $T_2$ decay amplitudes versus time, typically from 0.3 milliseconds to 3 seconds. The $T_2$ decay can be further processed to obtain pore volumes within particular ranges of $T_2$. The most common volumes are the bound fluid and free fluid. A permeability estimate from the relationship of the two fluids can then be made with an appropriate permeability transform such as the Timur-Coates or Kenyon (sometimes called SDR) equations. Note Kenyon, W. E., 1992, "Nuclear magnetic resonance as a petrophysical measurement", Nuclear Geophysics, 6, 153-171; and Timur, A., 1969, "Pulsed Nuclear Magnetic Resonance Studies of Porosity, Movable Fluid, and Permeability of Sandstones", *JPT*, 21, 775-786. A discussion of using magnetic resonance measurements specific to estimating permeability in gas hydrate reservoirs is provided in Murray, D., Fukuhara, M., Khong, C. K., Namikawa, T. and Yamamoto, K., 2006, "Permeability Estimates in Gas Hydrate Reservoirs of the Nankai Trough", 47th Annual SPWLA Symposium; and Kleinberg, R. L., Flaum, C. and Collett, T. S., 2005, "Magnetic resonance log of Mallik 5L38: Hydrate saturation, growth habit, and relative permeability", Scientific Results from the Mallik 2002 Gas Hydrate Production Research Well, Mackenzie Delta, Northwest Territories, Canada, Bulletin 585, Geological Survey of Canada, Ottawa, S. R. Dallimore and T. S. Collett (Editors).

Essentially the above papers demonstrate that in gas hydrate reservoirs the Kenyon approach is the most appropriate method to estimate gas hydrate reservoir permeability, with the proviso that the equation's input porosity is the total porosity as measured by magnetic resonance. As described by Kleinberg et al., 2005, in a gas hydrate saturated formation the magnetic resonance total porosity corresponds to the non-hydrate filled porosity only, or the permeable porosity portion. The magnetic resonance relaxation time $T_2$ of hydrate is so fast that magnetic resonance logging tools cannot measure it, they can only 'see' the non-hydrate filled porosity. Other logging devices like the formation density measurement tools can be used to measure total formation porosity (non-hydrate plus hydrate filled porosities). In a hydrate bearing rock, the difference between the total porosity as measured by the formation density and that by magnetic resonance very closely resembles the hydrate saturation, i.e., total formation porosity—total non-hydrate associated formation porosity. Note Murray, D., Kleinberg, R., Sinha, B., Fukuhara, M., Endo, T. and Narnikawa, T., 2005, "Formation Evaluation of Gas Hydrate Reservoirs", 46th Annual SPWLA Symposium.

As previously discussed above, alternative approaches which perform laboratory tests on retrieved cores suffer from an inability to maintain in-situ conditions, a situation that is particularly problematic in hydrate saturated rocks.

Referring to FIG. 3, in a method according to the present disclosure, a tool is deployed within a well hole (note flow diagram block 52). Magnetic resonance measurements at multiple depths 54 provide intrinsic permeabilities of the formation such that the measured permeabilities relate to different saturations of a gas hydrate zone of interest in the formation. Additionally, the latest generation of magnetic resonance logging tools like Schlumberger's MR Scanner (a trademark of Schlumberger) investigate the formation at multiple depths of investigation radially away from the borehole into the formation. The process of drilling a well through a hydrate saturated reservoir can cause small changes in the near wellbore temperature and pressure, and can cause small amounts of gas hydrate to dissociate. This dissociation alters the near wellbore hydrate saturation and thus the near wellbore permeability. The magnetic resonance derived permeability from multiple depths of investigation represents the permeability at different hydrate saturations. Correspondingly, hydrate saturations at the same depths of investigation as those mentioned above, can be derived from the difference between the magnetic resonance porosities at these depths of investigation and the total formation porosity as measured by the formation density.

Permeability of the formation at or near zero saturation of the hydrocarbon of interest is determined 56. Herron, M. M., Johnson, D. L., and Schwartz, L. M., 1998, "A Robust Permeability Estimator for Siliciclastics,", SPE 49301 paper presented at the 1998 Annual Technical Conference and Exhibition of the Society of Petroleum Engineers, New Orleans, La., 27-30 Sep., 1998, teach that in lithological sand-shale environments, where all known natural gas hydrate deposits are known to occur, the intrinsic permeability of a non-hydrate bearing formation can be estimated from geochemical logs. The geochemical approach is based on knowledge of a formation's lithology and total porosity. Its fundamental assumption is that the formation pore space is completely filled with fluids; oil, gas or water. It makes no allowance for the possibility that some of the pore space may be filled with a solid like gas hydrate. As such, in hydrate bearing rocks the estimated geochemical intrinsic permeability is equivalent to the permeability when no gas hydrate is present or zero hydrate saturation.

The dynamic relationship between permeability and gas hydrate saturation for the formation is determined 58 (note also FIG. 4).

A hydrate is a near impermeable solid, hydrate reservoirs have the unique property in that their permeability is heavily dependent on hydrate saturation. As hydrate is produced, less hydrate fills the pore space and as such overall reservoir permeability increases. To more fully understand hydrate reservoir behavior with production it is important to characterize the relationship between reservoir intrinsic permeability and hydrate saturation. FIG. 4 is a simulated plot of this relationship.

FIG. 4 shows a simulated relationship between intrinsic permeability and hydrate saturation for a generic sandstone. This relationship may be derived from a combination of in-situ measurements at multiple depths of investigation utilizing a suitable magnetic resonance tool, and geochemical measurements. The tools may be deployed in either wireline or slickline or logging-while-drilling (LWD) operational systems which are well known in the hydrocarbon drilling and production industry.

In one possible application of the techniques disclosed herein, during drilling small amounts of hydrate dissociation in the region near to the wellbore wall will cause a reduction in hydrate saturation, and correspondingly an increase in intrinsic permeability. The permeabilities derived from multiple depths of investigation utilizing magnetic resonance measurements in this near wellbore region represent permeabilities at different levels of hydrate saturation. From geochemical measurement it is possible to derive the reservoir rock's upper bound permeability for the case of no hydrate or 0% hydrate saturation.

In summary, the combination of the above measurements and related derivations described above provide in-situ measurements for the plot simulated in FIG. 4. The plot depicted in FIG. 4 represents a key characteristic of the hydrate saturated formation and is a key input to gas hydrate production simulators as it is known that the area of gas hydrate dissociation, and hence gas productivity, is significantly affected by permeability. Hence, knowledge of the dynamic relationship between permeability versus gas hydrate saturation influences the approach that is utilized for reservoir stimulation, i.e., thermal, depressurization, etc.

Although the present invention has been described in relation to particular embodiments thereof, other variations and modifications and other uses will become apparent to those skilled in the art. It is preferred, therefore, that the present invention be limited not by the specific disclosure herein, but only by the appended claims.

What is claimed is:

1. A method for determining dynamic permeability of gas hydrate formations by in-situ evaluation, comprising:
   deploying a tool within a wellhole configured for magnetic resonance measurements and measuring magnetic resonance porosities of a formation at multiple depths corresponding to different fluid saturations of a gas hydrate of interest in the formation;
   determining total formation porosities at the multiple depths;
   deriving gas hydrate saturations at the multiple depths from a difference between the corresponding total formation porosities and the magnetic resonance porosities at the multiple depths;
   determining magnetic resonance permeabilities at the multiple depths;
   determining permeability of the formation at or near zero saturation of the gas hydrate of interest;
   plotting the magnetic resonance permeabilities derived from multiple depths of investigation along the formation as a function of the gas hydrate saturations determined at the corresponding multiple depths; and
   using data obtained from plotting the magnetic resonance permeability as a function of the gas hydrate saturations as an input to a gas hydrate production simulator.

2. The method for determining dynamic permeability of gas hydrate formations as defined in claim 1, further comprising:
   estimating the magnetic resonance permeabilities of the formation using a Kenyon approach.

3. The method for determining dynamic permeability of gas hydrate formations as defined in claim 1, wherein:
   said gas hydrate of interest comprises methane hydrate.

4. The method for determining dynamic permeability of gas hydrate formations as defined in claim 1, wherein:

said tool comprises at least one of a wireline and a slickline tool.

5. The method for determining dynamic permeability of gas hydrate formations as defined in claim 1, wherein:
said tool is a logging-while-drilling (LWD) tool.

6. The method for determining dynamic permeability of gas hydrate formations as defined in claim 1, wherein:
the permeability of the formation at or near zero gas hydrate saturation is determined using geochemical measurements.

7. The method for determining dynamic permeability of gas hydrate formations as defined in claim 1, wherein:
data relating to said magnetic resonance measurements are transmitted to the surface for processing.

8. The method for determining dynamic permeability of gas hydrate formations as defined in claim 7, wherein:
said surface processing comprises real time processing of the data.

9. The method for determining dynamic permeability of gas hydrate formations as defined in claim 1, a formation density measuring tool is used to measure the total formation porosities.

10. A system for determining dynamic permeability of gas hydrate formations by in-situ evaluation, comprising:
a tool configured for magnetic resonance measurements within a wellhole to measure magnetic resonance porosities of a formation at multiple depths corresponding to different fluid saturations of a gas hydrate of interest in the formation;
a formation density measurement tool configured to determine total formation porosities at the multiple depths; and
a processor configured for determining permeability of the formation at or near zero saturation of the gas hydrate of interest and deriving the dynamic relationship between magnetic resonance permeability and gas hydrate saturation for the formation and wherein the processor communicates a plot of the magnetic resonance permeabilities as a function of the gas hydrate saturations, wherein the permeability of the formation at or near the zero saturation of the gas hydrate of interest is indicated by a magnetic resonance permeability measurement when a total formation porosity is substantially equal to a magnetic resonance porosity at a corresponding depth.

11. The system for determining dynamic permeability of gas hydrate formations as defined in claim 10, wherein:
said gas hydrate of interest comprises methane hydrate.

12. The system for determining dynamic permeability of gas hydrate formations as defined in claim 10, wherein:
said tool comprises at least one of a wireline and a slickline tool.

13. The system for determining dynamic permeability of gas hydrate formations as defined in claim 10, wherein:
said tool is a logging-while-drilling (LWD) tool.

14. The system for determining dynamic permeability of gas hydrate formations as defined in claim 10, wherein the system further comprises:
a tool configured to acquire geochemical measurements and the permeability of the formation at or near zero gas hydrate saturation is determined using the geochemical measurements.

15. The system for determining dynamic permeability of gas hydrate formations as defined in claim 10, wherein:
data relating to said magnetic resonance measurements are transmitted to the surface for processing.

16. The system for determining dynamic permeability of gas hydrate formations as defined in claim 15, wherein:
said surface processing comprises real time processing of the data.

17. A method for determining dynamic permeability of gas hydrate formations by in-situ evaluation comprising:
deploying a tool within a wellhole configured for magnetic resonance measurements and formation density measurements of a formation at multiple depths corresponding to different fluid saturations of a gas hydrate of interest in the formation;
determining total formation porosities and magnetic resonance porosities at the multiple depths;
deriving gas hydrate saturations at the multiple depths from a difference between the corresponding total formation porosities and the magnetic resonance porosities at the multiple depths;
determining magnetic resonance permeabilities at the multiple depths;
determining permeability of the formation at or near zero saturation of the gas hydrate of interest using geochemical measurements; and
creating a data plot of the permeabilities of the formation as a function of the gas hydrate saturations at corresponding depths; and
using the data plot as an input to a gas hydrate production simulator.

18. The method for determining dynamic permeability of gas hydrate formations as defined in claim 17, wherein:
said tool comprises at least one of a wireline and a slickline tool.

* * * * *